(12) United States Patent
Buescher et al.

(10) Patent No.: US 11,015,551 B2
(45) Date of Patent: May 25, 2021

(54) DEVICE FOR AN INTERNAL COMBUSTION ENGINE AND METHOD FOR OPERATING THE DEVICE

(71) Applicant: HELLA GmbH & Co. KGaA, Lippstadt (DE)

(72) Inventors: Ludger Buescher, Lippstadt (DE); Carsten Kuegeler, Lippstadt (DE); Ingo Niemeyer, Moehnesee (DE); Martin Meggle, Herzebrock-Clarholz (DE); Marco Unterhalt, Salzkotten (DE); Sven-Erik Wolf, Lippstadt (DE)

(73) Assignee: Hella GmbH & Co. KGaA, Lippstadt (DE)

( * ) Notice: Subject to any disclaimer, the term of this patent is extended or adjusted under 35 U.S.C. 154(b) by 19 days.

(21) Appl. No.: 16/439,241

(22) Filed: Jun. 12, 2019

(65) Prior Publication Data

US 2019/0376474 A1  Dec. 12, 2019

(30) Foreign Application Priority Data

Jun. 12, 2018 (DE) ............... 10 2018 113 995.0

(51) Int. Cl.
*F02M 25/08* (2006.01)
*F02M 23/00* (2006.01)
(Continued)

(52) U.S. Cl.
CPC ....... *F02M 25/0836* (2013.01); *F01N 3/0835* (2013.01); *F02M 23/00* (2013.01); *G01N 33/0062* (2013.01)

(58) Field of Classification Search
CPC .. F01N 3/0835; F02M 23/00; F02M 25/0836; G01N 33/0062
See application file for complete search history.

(56) References Cited

U.S. PATENT DOCUMENTS 4,116,184 A * 9/1978 Tomita ............... F02D 35/00
123/438
6,237,575 B1 * 5/2001 Lampert ............. F02D 41/0042
123/516

(Continued)

FOREIGN PATENT DOCUMENTS

DE   19813321 A1  10/1999
DE   102010061429 A1  6/2012
(Continued)

*Primary Examiner* — Phutthiwat Wongwian
*Assistant Examiner* — Diem T Tran
(74) *Attorney, Agent, or Firm* — Muncy, Geissler, Olds & Lowe, P.C.

(57) ABSTRACT

A device for an internal combustion engine for the combustion of a gasoline-based liquid fuel, having a tank, which is gas-conductively connected to the internal combustion engine with the aid of an exhaust gas line and a first shutoff valve, a hydrocarbon storage unit, which is gas-conductively disposed between the tank and the internal combustion engine with the aid of the exhaust gas line, for temporarily storing gaseous hydrocarbon contained in an exhaust gas escaping from the tank, and a hydrocarbon sensor, which is gas-conductively disposed between the tank and the internal combustion engine with the aid of the exhaust gas line, for measuring the hydrocarbon content in a purging air supplied to the internal combustion engine, the hydrocarbon storage unit being connectable to the free surroundings with the aid of a connecting line and a second shutoff valve.

15 Claims, 1 Drawing Sheet

(51) Int. Cl.
 *F01N 3/08* (2006.01)
 *G01N 33/00* (2006.01)

(56) References Cited

U.S. PATENT DOCUMENTS

| | | |
|---|---|---|
| 8,863,729 B2 | 10/2014 | Menke |
| 2017/0114732 A1* | 4/2017 | Dudar ................ F02M 25/0854 |
| 2017/0184057 A1 | 6/2017 | Weigl et al. |
| 2017/0204796 A1* | 7/2017 | Dudar ................... F02D 41/221 |
| 2018/0142634 A1* | 5/2018 | Sager .................. F02D 41/0032 |

FOREIGN PATENT DOCUMENTS

| | | |
|---|---|---|
| DE | 102014216454 A1 | 2/2016 |
| DE | 102015216504 A1 | 3/2017 |
| JP | 2007198267 * | 8/2007 |

\* cited by examiner

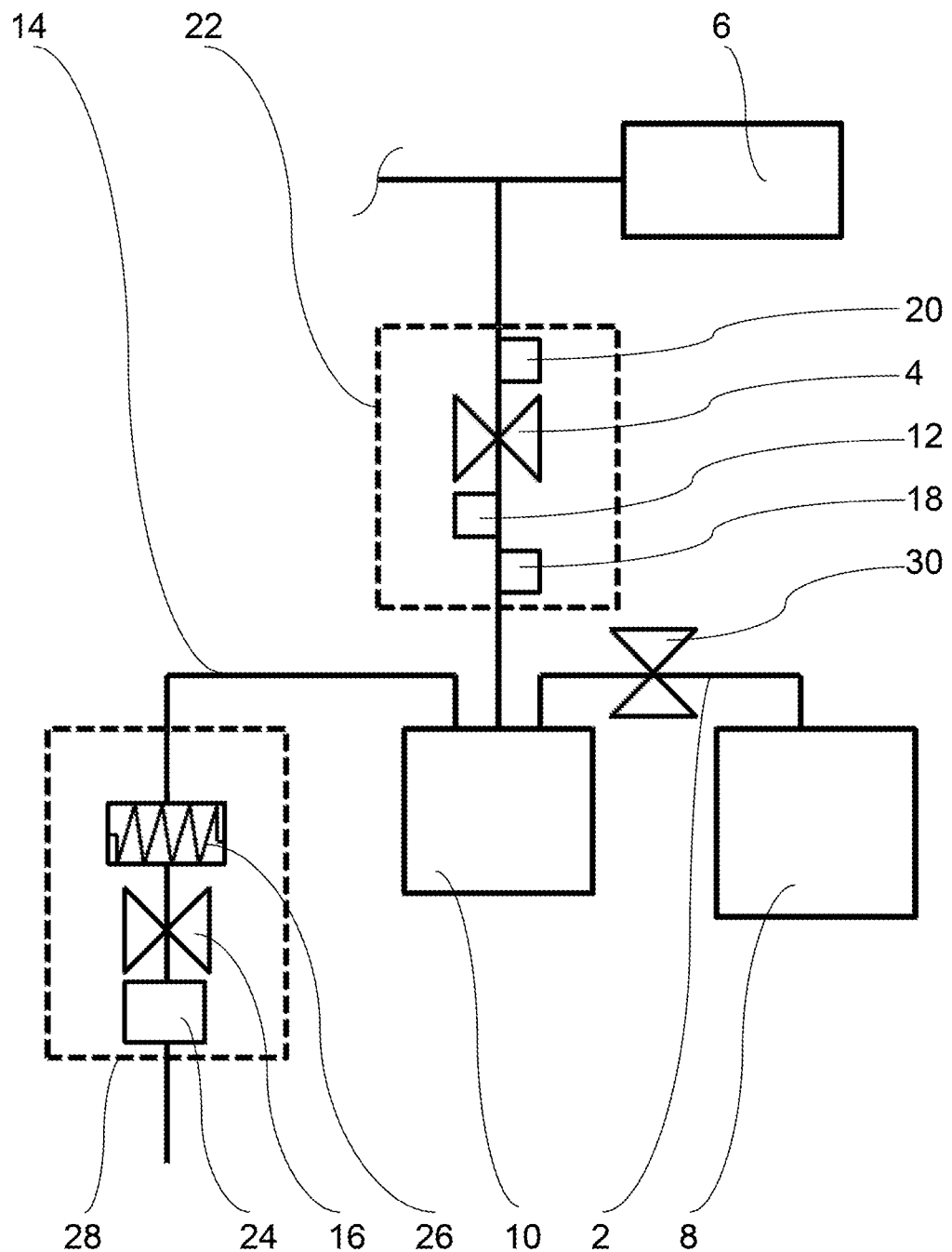

DEVICE FOR AN INTERNAL COMBUSTION ENGINE AND METHOD FOR OPERATING THE DEVICE

This nonprovisional application claims priority under 35 U.S.C. § 119(a) to German Patent Application No. 10 2018 113 995.0, which was filed in Germany on Jun. 12, 2018, and which is herein incorporated by reference.

BACKGROUND OF THE INVENTION

Field of the Invention

The present invention relates to a device for an internal combustion engine for the combustion of a gasoline-based liquid fuel of the type mentioned in the definition of the species in claim 1, as well as to a method for operating a device of this type.

Description of the Background Art

Devices of this type for an internal combustion engine for the combustion of a gasoline-based liquid fuel as well as methods for operating devices of this type are already known in numerous design variants from the prior art.

For example, a device for operating an internal combustion engine is known from DE 10 2008 060 250 A1. The known device includes a hydrocarbon storage unit for gaseous hydrocarbons, for the purpose of creating a tank venting system for a tank, having a reliable venting of the tank. This is intended to facilitate a precise emission of harmful substances, namely hydrocarbon, from the tank venting system. For the purpose of purging the hydrocarbon storage unit, the known device furthermore includes a first connection and a second connection, a valve, which suppresses a fluid flow of a fluid between the first connection and the second connection in a closed position and otherwise enables such flow, and a sensor, which is disposed on the first connection of the valve and is designed as a structural unit with the valve, for detecting the concentration of hydrocarbon in the fluid. The fluid is supplied to the internal combustion engine during the purging of the hydrocarbon storage unit. The additional supply of combustion air and fuel to the internal combustion engine is to be adapted by detecting the concentration of gaseous hydrocarbon in the fluid. Moreover, the known device is connected to the free surroundings, i.e. the ambient air, with the aid of a line for the purpose of pressure compensation of the tank.

SUMMARY OF THE INVENTION

It is therefore an object of the present invention to improve the device known from the prior art and the operation thereof.

In an exemplary embodiment, this object is achieved by a device for an internal combustion engine for the combustion of a gasoline-based liquid fuel having a tank, which is gas-conductively connected to the internal combustion engine with the aid of an exhaust gas line and a first shutoff valve, a hydrocarbon storage unit, which is gas-conductively disposed between the tank and the internal combustion engine with the aid of the exhaust gas line for temporarily storing gaseous hydrocarbons contained in an exhaust gas escaping from the tank, and a hydrocarbon sensor, which is gas-conductively situated between the tank and the internal combustion engine with the aid of the exhaust gas line for measuring the hydrocarbon content in a purging air supplied to the internal combustion engine, the hydrocarbon storage unit being connectable to the free surroundings with the aid of a connecting line and a second shutoff valve. The device according to the invention is characterized in that the device includes exactly one pump, the pump being designed and disposed in operative connection to the first and second shutoff valves, on the one hand for generating an overpressure or an underpressure in the exhaust gas line or the exhaust gas line and the tank, and on the other hand for transporting purging air, formed from ambient air sucked in from the surroundings with the aid of the connecting line and the hydrocarbon temporarily stored in the hydrocarbon storage unit, from the hydrocarbon storage unit to the internal combustion engine.

The object is also achieved by a method for operating a device according to the invention, the method including at least the following method steps: generating overpressure or underpressure in the exhaust gas line or the exhaust gas line and the tank with the aid of the pump for the purpose of diagnosing a leak in the exhaust gas line or the exhaust gas line and the tank in a leak detection mode of the device, and transporting ambient air through the hydrocarbon storage unit with the aid of the connecting line and the pump for the purpose of purging the hydrocarbon storage unit, and supplying purging air formed from this ambient air with the hydrocarbon temporarily stored in the hydrocarbon storage unit to the internal combustion engine in a purging mode of the device.

An essential advantage of the invention is, in particular, that the different functions of the purging of the hydrocarbon storage unit, on the one hand, and the detection of a leak in the exhaust gas line or in the exhaust gas line and the tank, on the other hand, may be easily implemented. This is due to the fact that an extensive integration of the two functions, namely the purging of the hydrocarbon storage unit and the detection of leaks, is facilitated with the aid of the device according to the invention and the method according to the invention. Synergies may be advantageously used accordingly.

A pump is generally freely selectable within broad, suitable limits, depending on the type, material, functionality, dimensioning and arrangement. An advantageous refinement of the device according to the invention provides that the pump is disposed in the connecting line. In this way, an explosion protection for the one pump may be particularly easily implemented, since only ambient air from the free surroundings, i.e. fresh air, is sucked in with the aid of the connecting line and the one pump disposed in the connecting line.

The pump can be disposed in the exhaust gas line between the internal combustion engine and the hydrocarbon storage unit. This makes it possible to provide the one pump with a particularly simple design. For example, the pump may be designed only to achieve an underpressure. With the aid of underpressure generated by the pump, it is possible to purge the hydrocarbon storage unit and also check the exhaust gas line or the exhaust gas line and the tank for a leak. It is therefore not absolutely necessary for the pump disposed in this manner to be able to generate both overpressure and underpressure. Moreover, this arrangement of the one pump has the advantage that the pump is disposed in the engine compartment. Accordingly, sufficient installation space is available. In addition, the acoustics, namely the reduction of undesirable noise emissions, is very easily improved hereby. Due to the local proximity to the internal combustion engine, the regulation, namely the control speed, is improved in the one pump.

The pump can form a structural unit with the first shutoff valve and/or the hydrocarbon sensor. The compactness of the device according to the invention is improved in this manner. In addition, the electrification as well as the electrical/electronic connection of the pump to a vehicle control system with the aid of the first shutoff valve and/or the hydrocarbon sensor is simplified, and a reduction of the material complexity is facilitated.

As already explained above, the one pump is freely selectable within broad, suitable limits. Another advantageous refinement of the device according to the invention provides that the pump is designed as a dynamic pump. Dynamic pumps are available in a great many specific embodiments and may thus be used for a large number of different applications. Dynamic pumps are also robust and economical. If the one pump is disposed in the connecting line, the design as a dynamic pump additionally has the advantage that a venting of the exhaust gas line or the exhaust gas line and the tank may be particularly easily implemented. The pressure compensation may easily take place with the aid of the dynamic pump, for example without the latter being in operation.

The device can also include a pressure sensor and/or a temperature sensor and/or a mass flow sensor, the pressure sensor and/or the temperature sensor and/or the mass flow sensor being preferably disposed in the exhaust gas line, particularly preferably between the internal combustion engine and the hydrocarbon storage unit. This makes it possible, on the one hand, for the hydrocarbon sensor to be designed as a relative hydrocarbon sensor. With the aid of the pressure sensor and/or the temperature sensor and/or the mass flow sensor, the absolute hydrocarbon content of the purging air is then ascertainable in the manner known to those skilled in the art. With the aid of the mass flow sensor, it is furthermore possible to ascertain the proportion of air in the purging air and thus also take it into account in regulating the internal combustion engine. The more precise and faster the ascertainment of the hydrocarbon content or the hydrocarbon content and the air in the purging air, the more precise and faster can the internal combustion engine as a whole be regulated. With the aid of a precise and fast regulation of the internal combustion engine, the efficiency of the internal combustion engine is improved, on the one hand, and undesirable harmful substances, which are discharged into the surroundings upon an incomplete combustion, are effectively reduced, on the other hand.

The pressure sensor and/or the temperature sensor and/or the mass flow sensor can form a structural unit with the hydrocarbon sensor. The degree of integration of the individual components of the device according to the invention is further increased in this manner. The compactness of the device according to the invention as well as the electrification and the electrical/electronic connection of the individual components of the device according to the invention to the vehicle control system are therefore further improved.

A heating element and/or an air ionizer can be disposed in the connecting line. The efficiency of the purging of the hydrocarbon storage unit with the aid of ambient air sucked in from the surroundings, i.e. fresh air, is improved hereby.

In principle, the method according to the invention is freely selectable within broad, suitable limits.

The leak detection mode can be automatically started only in a non-operating mode of the internal combustion engine. In this way, an undesirable influencing of the internal combustion engine and its regulation when carrying out the detection of leaks in the exhaust gas line or in the exhaust gas line and the tank is particularly easily prevented.

The purge mode can be automatically started only in an operating mode of the internal combustion engine. This effectively prevents, at least, however, effectively reduces, an undesirable discharge of harmful substances into the surroundings, i.e. into the ambient air. In addition, the energy contained in the gaseous hydrocarbon of the purging air is made largely usable for operating the internal combustion engine and thus effectively reduces the consumption of additional energy from fuel, i.e., for example, from gasoline-based liquid fuel.

Further, in a venting mode of the device, exhaust gas from the tank can be removed from hydrocarbon with the aid of the hydrocarbon storage unit, and the exhaust gas removed from hydrocarbon is discharged into the free surroundings with the aid of the connecting line. On the one hand, the necessary pressure compensation of the exhaust gas line or the exhaust gas line and the tank is ensured in this manner. On the other hand, this effectively prevents the hydrocarbon contained in the exhaust gas from the exhaust gas line or the exhaust gas line and the tank from undesirably entering the surroundings, i.e. the ambient air. The venting may take place with or without the support of the pump.

A third shutoff valve can be disposed in the exhaust gas line between the tank and the hydrocarbon storage unit. This makes it possible to disconnect the tank for the hydrocarbon storage unit in a desirable manner. For example, it is conceivable that the tank is automatically connectable to the hydrocarbon storage unit only in predefined non-operating states and/or in operating states of the internal combustion engine. This is advantageous, in particular, in vehicles for countries or regions, in which the fuel dispensers of the filling stations do no have any extraction devices which automatically extract the exhaust gases escaping from the tank during a fueling operation.

Also, a generally closed third shutoff valve is automatically opened and the venting mode is automatically started only during a fueling operation for filling the tank with gasoline-based liquid fuel.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given hereinbelow and the accompanying drawings which are given by way of illustration only, and thus, are not limitive of the present invention, and wherein the sole FIGURE shows an exemplary embodiment of a device according to the invention.

DETAILED DESCRIPTION

An exemplary embodiment of a device according to the invention for an internal combustion engine for the combustion of a gasoline-based liquid fuel is shown by way of example in the FIGURE. The device comprises a tank 8 for the gasoline-based liquid fuel, which is gas-conductively connected to internal combustion engine 6 with the aid of an exhaust gas line 2 and a first shutoff valve 4, a hydrocarbon storage unit 10, which is gas-conductively disposed between tank 8 and internal combustion engine 6 with the aid of exhaust gas line 2, for temporarily storing gaseous hydrocarbon contained in an exhaust gas escaping from tank 8, and a hydrocarbon sensor 12, which is gas-conductively disposed between tank 8 and internal combustion engine 6 with the aid of exhaust gas line 2, for measuring the hydrocarbon content in a purging air supplied to internal combustion engine 6, the hydrocarbon storage unit 10 being connectable to the free surroundings with the aid of a connecting line 14 and a second shutoff valve 16. Hydrocarbon storage unit 10 is designed as an activated carbon filter 10.

First shutoff valve 4 and hydrocarbon sensor 12 are combined into a structural unit with a combined pressure and temperature sensor 18 and a mass flow sensor 20. In FIG. 1, this structural unit is symbolized with the aid of a dashed border 22.

The device also includes exactly one pump 24 designed as a dynamic pump, pump 24 being designed and disposed in operative connection to first and second shutoff valves 4, 16, on the one hand for generating an overpressure in exhaust gas line 2 and tank 8, and on the other hand for transporting purging air, formed from ambient air sucked in from the surroundings with the aid of connecting line 14 and the hydrocarbon temporarily stored in hydrocarbon storage unit 10, from hydrocarbon storage unit 10 to internal combustion engine 6. Pump 24 is disposed in connecting line 14 and forms a structural unit with second shutoff valve 16 and a heating element 26. In FIG. 1, this structural unit is symbolized with the aid of a dashed border 28. Pump 24 is designed to generate an overpressure or a slight underpressure in exhaust gas line 2 and tank 8 in a desired manner. This is easily implemented, due to the design of pump 24 as a dynamic pump.

A third shutoff valve 30 is disposed in exhaust gas line 2 between tank 8 and hydrocarbon storage unit 10. With the aid of third shutoff valve 30, it is possible to isolate tank 8 from the rest of the device according to the invention according to the present exemplary embodiment, so that the escape of exhaust gas enriched with gaseous hydrocarbon from tank 8 into exhaust gas line 2 may be controlled or regulated with the aid of third shutoff valve 30.

The method according to the invention is explained in greater detail below according to the present exemplary embodiment, based on FIG. 1.

Internal combustion engine 6 of a vehicle equipped with the device according to the invention, according to the above explanations, is in a non-operating mode of internal combustion engine 6. The vehicle is not illustrated. Internal combustion engine 6 is not in operation. The non-operating mode of internal combustion engine 6 is automatically detected in a manner known to those skilled in the art, and a vehicle control system of the vehicle, automatically places the device into its leak detection mode according to the present exemplary embodiment. In the leak detection mode of the device, first shutoff valve 4 is initially closed, and ambient air is sucked in from the surroundings and transported to exhaust gas line 2 with the aid of pump 24 and connecting line 14 while second shutoff valve 16 is open. To check not only exhaust gas line 2 for a possible leak, third shutoff valve 30 is opened, so that tank 8 is gas-conductively connected to exhaust gas line 2. The pressure in the gas chamber formed from exhaust gas line 2, connecting line 14 and tank 8 is detected with the aid of combined pressure/temperature sensor 18 and transmitted to the vehicle control system for evaluation. Once a predefined pressure for the leak detection has been reached, second shutoff valve 16 is closed, so that the gas chamber formed by exhaust gas line 2, connecting line 14 and tank 8 is also cut off from the surroundings. To be able to preferably completely check exhaust gas line 2 for leaks, first shutoff valve 4 is disposed in exhaust gas line 2, preferably close to its end facing the internal combustion engine. This also applies to the arrangement of second shutoff valve 16 in connecting line 14. Once a leak has been detected in the aforementioned manner in the gas chamber formed by exhaust gas line 4, connecting line 14 and tank 8, a warning may be issued in the manner known to those skilled in the art with the aid of a user interface. Other vehicle actions known to those skilled in the art are also conceivable.

If no leak has been detected in the gas chamber formed from exhaust gas line 4, connecting line 14 and tank 8, a user of the vehicle may place internal combustion engine 6 into operation. Internal combustion engine 6 is thus placed from the non-operating mode into an operating mode in the manner known to those skilled in the art. If hydrocarbon storage unit 10 is loaded with hydrocarbon to a predefined degree, for example saturated, the purge mode of the device according to the invention is now started automatically according to the present exemplary embodiment, i.e. in the operating mode of internal combustion engine 6. Ambient air is sucked in from the surroundings with the aid of pump 24, conducted through hydrocarbon storage unit 10 via connecting line 14 and transported to internal combustion engine 6 via exhaust gas line 2. The ambient air in hydrocarbon storage unit 10 absorbs hydrocarbons from hydrocarbon storage unit 10, so that purging air formed from the ambient air and the hydrocarbon absorbed from the ambient air is transported to internal combustion engine 6 via exhaust gas line 2. Accordingly, first and second shutoff valves 4, 16 are opened in the purge mode of the device. With the aid of hydrocarbon sensor 12, combined pressure/temperature sensor 18 and mass flow sensor 20, it is now possible to ascertain the quantities of gaseous hydrocarbon and air supplied to internal combustion engine 6 with the aid of the purging air and to use them to regulate internal combustion engine 6 in the manner known to those skilled in the art. For example, the quantities of hydrocarbon and air ascertained in this manner are used to regulate the additional supply of ambient air from the free surroundings and the additional supply of gasoline-based liquid fuel from tank 8. In the present exemplary embodiment, third shutoff valve 30 is, in principle, closed in the operating mode of internal combustion engine 6 and thus isolates tank 8 in the operating mode of internal combustion engine 6 from the rest of the device according to the invention according to the present exemplary embodiment. The ambient air sucked in with the aid of pump 24 in purge mode is preheated with the aid of heating element 26 to thereby favor the purging of hydrocarbon storage unit 10, i.e. unloading hydrocarbon therefrom.

If the vehicle is being fueled at a fuel pump of a filling station, the exhaust gas displaced by gasoline-based liquid fuel during the filling of tank 8 must be discharged to prevent an undesirable formation of overpressure in tank 8. For this purpose, the device according to the invention is automatically placed into its venting mode according to the present exemplary embodiment upon the commencement of the fueling operation. Third shutoff valve 30 is opened, so that the exhaust gas loaded with gaseous hydrocarbon, due to the filling of tank 8, is able to flow into hydrocarbon storage unit 10 with the aid of exhaust gas line 2. The gaseous hydrocarbon is removed from the exhaust gas with the aid of hydrocarbon storage unit 10, and the exhaust gas from which hydrocarbon has been removed in this manner may then be discharged into the surroundings with the aid of connecting line 14, opened second shutoff valve 16 and pump 24. After the filling of tank 8, third shutoff valve 30 may be automatically closed again. If hydrocarbon storage unit 10 is loaded with hydrocarbon to the predefined degree explained above, the device according to the invention is then placed into its purge mode—if internal combustion engine 6 is in an operating mode—according to the present exemplary embodiment. Refer to the explanations above.

The invention is not limited to present exemplary embodiment. For example, it is possible for the vehicle having the internal combustion engine to additionally include an electric motor and/or a gas motor. Instead of disposing the pump in the connecting line, it is also conceivable that the pump is disposed in the exhaust gas line between the internal combustion engine and the hydrocarbon storage unit. In the last-mentioned specific embodiment of the device according to the invention, for example, it would be possible for the pump to form a structural unit with the first shutoff valve and/or the hydrocarbon sensor. The pressure sensor and the temperature sensor do not have to be designed as a combined pressure/temperature sensor. For example, a separate pressure sensor and a separate temperature sensor would also be possible. Instead of the structural units explained in the exemplary embodiment, other structural units could also be formed, depending on the requirements of the individual case. For example, the hydrocarbon sensor and/or the pressure sensor and/or the temperature sensor could also be combined into a structural unit with the hydrocarbon storage unit. Alternatively or in addition to a pressure sensor in the exhaust gas line, it would also be conceivable to dispose a pressure sensor in the connecting line. For example, the pressure sensor could then be integrated into a structural unit with the pump disposed in the connecting line and/or the second shutoff valve and/or the heating element. The purging of the hydrocarbon storage unit could also be supported by an air ionizer disposed in the connecting line instead of the heating element or in addition to the heating element. The third shutoff valve is not absolutely necessary. Accordingly, specific embodiments are also possible, in which the tank is continuously connected to the hydrocarbon storage unit with the aid of the exhaust gas line. This is conceivable, for example, in vehicles for countries or regions, in which the fuel pumps have an automatic discharge of exhaust gas loaded with gaseous hydrocarbon during a filling of the tank with liquid fuel. The hydrocarbon sensor may be designed for both relative and absolute measurement. If the hydrocarbon sensor is designed for absolute measurement, at least a portion of the additional sensor system formed from the pressure sensor, temperature sensor and mass flow sensor may be dispensed with. Instead of an overpressure, an underpressure may also be generated and used for the leak detection mode with the aid of the one pump. If the one pump is to be designed for both generating underpressure and for generation overpressure in the exhaust gas line or the exhaust gas line and the tank, it is conceivable that the pump is alternately connectable to the exhaust gas line by its delivery side and its suction side, for example with the aid of a valve block or the like.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for an internal combustion engine for combustion of a gasoline-based liquid fuel, the device comprising:
    a tank that is gas-conductively connected to the internal combustion engine via an exhaust gas line and a first shutoff valve;
    a hydrocarbon storage unit that is gas-conductively disposed between the tank and the internal combustion engine via the exhaust gas line, for temporarily storing gaseous hydrocarbon contained in an exhaust gas escaping from the tank;
    a hydrocarbon sensor that is gas-conductively disposed between the tank and the internal combustion engine via the exhaust gas line, for measuring a hydrocarbon content in a purging air supplied to the internal combustion engine, the hydrocarbon storage unit being connectable to the free surroundings via a connecting line and a second shutoff valve;
    exactly one pump being in operative connection with the first and second shutoff valves for generating an overpressure or an underpressure in the exhaust gas line or the exhaust gas line and the tank and being in operation to transport the purging air from the hydrocarbon storage unit to the internal combustion engine, wherein the purging air is formed from ambient air sucked in from the free surroundings via the connecting line and the hydrocarbon temporarily stored in the hydrocarbon storage unit, and
    a pressure sensor, a temperature sensor and a mass flow sensor, the pressure sensor, the temperature sensor and the mass flow sensor being disposed in the exhaust gas line between the internal combustion engine and the hydrocarbon storage unit to ascertain the absolute hydrocarbon content of the purging air.

2. The device according to claim 1, wherein the pump is disposed in the connecting line.

3. The device according to claim 1, wherein the pump is disposed in the exhaust gas line between the internal combustion engine and the hydrocarbon storage unit.

4. The device according to claim 3, wherein the pump forms a structural unit with the first shutoff valve and/or the hydrocarbon sensor.

5. The device according to claim 1, wherein the pump is a dynamic pump.

6. The device according to claim 1, wherein the pressure sensor and/or the temperature sensor and/or the mass flow sensor form a structural unit with the hydrocarbon sensor.

7. The device according to claim 1, wherein a heating element and/or an air ionizer is/are disposed in the connecting line.

8. The device according to claim 1, wherein a third shutoff valve is disposed in the exhaust gas line between the tank and the hydrocarbon storage unit.

9. A method for operating a device according to claim 1, the method comprising:
    generating overpressure or underpressure in the exhaust gas line or the exhaust gas line and the tank via the pump for diagnosing a leak in the exhaust gas line or the exhaust gas line and the tank in a leak detection mode of the device;
    transporting ambient air through the hydrocarbon storage unit via the connecting line and via operation of the pump for purging the hydrocarbon storage unit and supplying the purging air, formed from the ambient air and the temporarily stored hydrocarbon in the hydrocarbon storage unit, to the internal combustion engine in a purge mode of the device.

10. The method as recited in claim 9, wherein the leak detection mode is automatically started only in a non-operating mode of the internal combustion engine.

11. The method as recited in claim 9, wherein the purge mode is automatically started only in an operating mode of the internal combustion engine.

12. The method as recited in claim 9, wherein, in a venting mode of the device, hydrocarbon in the exhaust gas from the tank is removed via the hydrocarbon storage unit, and wherein the exhaust gas, after removal of the hydrocarbon, is discharged into the free surroundings via the connecting line.

13. The method according to claim 12, wherein a generally closed third shutoff valve is automatically opened and the venting mode is automatically started only during a fueling operation for filling the tank with gasoline-based liquid fuel.

14. The method according to claim 1, wherein a heating element is disposed in the connecting line, the heating element being integrated in a structural unit that includes the second shutoff valve and the pump.

15. The method according to claim 1, wherein a mass flow sensor, the first shut off valve, the hydrocarbon sensor, a pressure sensor and a temperature sensor are integrated in a structural unit.

\* \* \* \* \*